United States Patent
Liao (10) Patent No.: US 12,115,016 B2
(45) Date of Patent: Oct. 15, 2024

(54) THERAPEUTIC APPARATUS AND ALIGNMENT METHOD AND DEVICE THEREOF

(71) Applicant: BOE TECHNOLOGY GROUP CO., LTD., Beijing (CN)

(72) Inventor: Pingping Liao, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 564 days.

(21) Appl. No.: 17/417,499

(22) PCT Filed: Dec. 28, 2020

(86) PCT No.: PCT/CN2020/140252
§ 371 (c)(1),
(2) Date: Jun. 23, 2021

(87) PCT Pub. No.: WO2021/184890
PCT Pub. Date: Sep. 23, 2021

(65) Prior Publication Data
US 2022/0346744 A1    Nov. 3, 2022

(30) Foreign Application Priority Data

Mar. 19, 2020   (CN) .......................... 202010198453.5

(51) Int. Cl.
*A61B 17/00* (2006.01)
*A61B 6/00* (2006.01)
(Continued)

(52) U.S. Cl.
CPC ............ *A61B 6/547* (2013.01); *A61B 6/4441* (2013.01); *G06T 7/70* (2017.01); *G06T 7/80* (2017.01)

(58) Field of Classification Search
CPC .................... A61B 6/547; A61B 34/30; A61B 2017/00725; A61B 90/50;
(Continued)

(56) References Cited

U.S. PATENT DOCUMENTS 5,967,982 A * 10/1999 Barnett ................. A61B 34/20
606/130
10,166,080 B2   1/2019 Balicki et al.
(Continued)

FOREIGN PATENT DOCUMENTS

CN          1950035 A    4/2007
CN        101242787 A    8/2008
(Continued)

OTHER PUBLICATIONS

China Patent Office, First Office Action issued Nov. 4, 2020 for application No. CN202010198453.5.
(Continued)

*Primary Examiner* — David P Porta
*Assistant Examiner* — Mamadou Faye
(74) *Attorney, Agent, or Firm* — HOUTTEMAN LAW LLC (57) ABSTRACT

A therapeutic apparatus includes an image capturing mechanism and a mechanical arm, and further includes a calibration plate on which a calibration plane is defined. The mechanism includes reference plate and image capturing element with adjustable capturing direction, the capturing element is opposite to and spaced apart from reference plate, and a surface of reference plate facing the capturing element is defined as reference plane. The arm includes a body, a fixed end and an operating end, the fixed and operating ends are located at different positions of the body, respectively, the body is fixed to mounting base through fixed end, the calibration plate is arranged at operating end, and the body
(Continued)

is driven to move operating end to a position between capturing element and reference plate such that the calibration plate is parallel to calibration plane and reference plane.

19 Claims, 5 Drawing Sheets

(51) Int. Cl.
  *G06T 7/70* (2017.01)
  *G06T 7/80* (2017.01)
(58) Field of Classification Search
  CPC . A61B 2090/376; A61B 6/4441; A61B 6/505; A61B 17/8866; A61B 34/20; A61B 34/70; A61B 2034/2065; A61B 2034/2068; G06T 7/70; G06T 7/80
  See application file for complete search history.

(56) References Cited

U.S. PATENT DOCUMENTS

| | | | |
|---|---|---|---|
| 2016/0361125 A1 | 12/2016 | Balicki et al. | |
| 2019/0142359 A1* | 5/2019 | Zhang | A61B 34/20 606/130 |

FOREIGN PATENT DOCUMENTS

| | | |
|---|---|---|
| CN | 105963018 A | 9/2016 |
| CN | 107049488 A | 8/2017 |
| CN | 107468350 A | 12/2017 |
| CN | 107767423 A | 3/2018 |
| CN | 108042173 A | 5/2018 |
| CN | 109345578 A | 2/2019 |
| CN | 109620274 A | 4/2019 |
| CN | 111388089 A | 7/2020 |

OTHER PUBLICATIONS

China Patent Office, Second Office Action issued Mar. 31, 2021 for application No. CN202010198453.5.
China Patent Office, Decision of Rejection issued Sep. 8, 2021 for application No. CN202010198453.5.

* cited by examiner

```
┌─────────────────────────────────────────────────────────┐
│ Drive to move mechanical arm body, so as to move        │
│ calibration plate to position between image capturing   │
│ element and reference plane, wherein calibration plane  │
│ is parallel to reference plane, calibration plane is    │
│ located at level of treatment site, and angle between   │
│ the reference plane and horizontal plane is             │
│ predetermined angle                                     │
└─────────────────────────────────────────────────────────┘
                            │  S110
                            ▼
┌─────────────────────────────────────────────────────────┐
│      Control image capturing element to obtain image    │
└─────────────────────────────────────────────────────────┘
                            │  S120
                            ▼
┌─────────────────────────────────────────────────────────┐
│ Determine, according to position of the calibration     │
│ plane in the obtained image, alignment relationship     │
│ between coordinate system of image and coordinate       │
│ system of mechanical arm                                │
└─────────────────────────────────────────────────────────┘
                                                   S130
```

THERAPEUTIC APPARATUS AND ALIGNMENT METHOD AND DEVICE THEREOF

This application is a National Phase Application filed under 35 U.S.C. 371 as a national stage of PCT/CN2020/140252, filed on Dec. 28, 2020, an application claiming the priority of the Chinese patent application No. 202010198453.5, filed on Mar. 19, 2020, the contents of which are incorporated herein by reference in their entirety.

FIELD OF THE INVENTION

The present disclosure relates to the field of medical apparatus and instruments, and in particular, to a therapeutic apparatus, an alignment method of the therapeutic apparatus, and an alignment device of the therapeutic apparatus.

BACKGROUND

With the development of artificial intelligence, robots for treatment have appeared. However, for orthopedic treatment, robots have not been widely used.

In particular, orthopedic treatments include fracture reduction. Furthermore, fracture reduction includes both open reduction and closed reduction. Compared with the open reduction, the closed reduction has the advantages of no wound, quick recovery, low cost and the like. Particularly during the closed reduction, a reliable robot application is not available, and it is greatly depended on the experience of a doctor.

SUMMARY

The disclosure is to provide a therapeutic apparatus, an alignment method of the therapeutic apparatus, and an alignment device of the therapeutic apparatus.

As a first aspect of the disclosure, there is provided a therapeutic apparatus, including an image capturing mechanism and a mechanical arm, wherein the therapeutic apparatus further includes a calibration plate, on which a calibration plane is defined;
- the image capturing mechanism includes a reference plate and an image capturing element with an adjustable capturing direction, the image capturing element is opposite to and spaced apart from the reference plate, and a surface of the reference plate facing the image capturing element is defined as a reference plane; and
- the mechanical arm includes a mechanical arm body, a fixed end and an operating end, the fixed end and the operating end are located at different positions of the mechanical arm body, respectively, the mechanical arm body is able to be fixed to a mounting base through the fixed end, the calibration plate is arranged at the operating end, and the mechanical arm body is able to drive to move the operating end to a position between the image capturing element and the reference plate such that the calibration plate is driven to move to be parallel to the calibration plane and the reference plane.

Optionally, the calibration plate includes a calibration plate substrate and a plurality of calibration members disposed on the calibration plate substrate, and the plurality of calibration members define the calibration plane.

Optionally, the plurality of the calibration members include a first calibration member, a second calibration member, and a third calibration member, and a first line between the first calibration member and the second calibration member is perpendicular to a third line between the second calibration member and the third calibration member.

Optionally, the calibration plate substrate is a transparent substrate, and the calibration member is embedded in the calibration plate substrate.

Optionally, the image capturing element is an X-ray image capturing element, and each calibration member is a metal ball.

Optionally, the therapeutic apparatus further comprises a clamp disposed at the operating end of the mechanical arm.

Optionally, the image capturing mechanism further includes a mounting bracket on which the image capturing element and the reference plate are mounted.

Optionally, the mounting bracket is able to drive to move the image capturing element and the reference plate to change an orientation of the image capturing element, and when the image capturing element and the reference plate are moved, a relative positional relationship between the image capturing element and the reference plate is kept unchanged.

Optionally, the mounting bracket includes a base and a mounting arm disposed on the base, the mounting arm includes a mounting arm body, a mounting end of reference plate formed on the mounting arm body and a mounting end of the image capture element formed on the mounting arm body, the mounting end of the reference plate is disposed opposite to and spaced apart from the mounting end of the image capture element, the reference plate is mounted on the mounting end of the reference plate, and the image capture element is mounted on the mounting end of the image capture element.

Optionally, the mounting arm body is formed as an arc-shaped rod, the mounting end of the image capturing element is located at an end of the mounting arm body, the mounting end of the reference plate is located at the other end of the mounting arm body, and the mounting arm body is rotatable around a center of the mounting arm body to change the orientation of the image capturing element.

Optionally, one of the base and the mounting arm body is formed with a sliding slot and the other one of the base and the mounting arm body is formed with a projection that matches with the slide slot, allowing the mounting arm body to rotate on the base about a center of the mounting arm body.

As a second aspect of the disclosure, there is provided an alignment method applied to the above therapeutic apparatus according to the disclosure, wherein the alignment method includes:
- driving to move the mechanical arm body, so as to move the calibration plate to a position between the image capturing element and the reference plane, wherein the calibration plane is parallel to the reference plane and located at a level of a treatment site, and an angle between the reference plane and the horizontal plane is a first angle;
- controlling the image capturing element to obtain an image; and
- determining, according to a position of the calibration plane in the obtained image, an alignment relationship between a coordinate system of the image and a coordinate system of the mechanical arm, wherein the coordinate system of the mechanical arm is arranged at the fixed end of the mechanical arm, and a plane X-Y in the coordinate system of the mechanical arm is the horizontal plane.

Optionally, the image capturing element is an X-ray image capturing element, each calibration member is a metal ball, and the step of d determining, according to the position of the calibration plane in the obtained image, the alignment relationship between the coordinate system of the image and the coordinate system of the mechanical arm includes:

determining joint angle information of the mechanical arm body;

determining coordinates of a spherical center of each calibration member in the coordinate system of the image;

calculating coordinates of the spherical center of each calibration member in the coordinate system of the mechanical arm; and determining, by coordinate transformation, the alignment relationship between the coordinate system of the image and the coordinate system of the mechanical arm, wherein the alignment relationship is characterized by a translation parameter of the coordinate system of the image relative to the coordinate system of the mechanical arm, a rotation parameter of the coordinate system of the image relative to the coordinate system of the mechanical arm, and scaling of the image.

Optionally, the first angle is 0°, and in the step of calculating coordinates of the spherical center of each calibration member in the coordinate system of the mechanical arm, X and Y coordinates of the spherical center of the calibration member in the coordinate system of the mechanical arm are calculated.

Optionally, the step of determining, by the coordinate transformation, the alignment relationship between the coordinate system of the image and the coordinate system of the mechanical arm comprises:

determining the translation parameter by equation (1):

$$\begin{bmatrix} D_x \\ D_y \end{bmatrix} = \begin{bmatrix} x_{p2} \\ y_{p2} \end{bmatrix} - \begin{bmatrix} x_{r2} \\ y_{r2} \end{bmatrix} \quad (1)$$

calculating the rotation parameter by equations (2) to (4):

$$\theta = A - a \quad (2)$$

$$A = \arctan\left[\frac{y_{p3} - y_{p2}}{x_{p3} - x_{p2}}\right] \quad (3)$$

$$a = \arctan\left[\frac{y_{r3} - y_{r2}}{x_{r3} - x_{r2}}\right] \quad (4)$$

calculating the scaling of the image by equation (5):

$$\alpha = \frac{|x_{p2}|}{L} \quad (5)$$

wherein $D_x$ is a translation distance of x coordinate of the coordinate system of the image relative to x coordinate of the coordinate system of the mechanical arm, and $D_y$ is a translation distance of y coordinate of the coordinate system of the image relative to y coordinate of the coordinate system of mechanical arm;

$x_{p2}$ is an x-axis coordinate of the second calibration member in the coordinate system of the image;

$x_{r2}$ is an x-axis coordinate of the second calibration member in the coordinate system of the mechanical arm;

$y_{p2}$ is a y-axis coordinate of the second calibration member in the coordinate system of the image;

$y_{r2}$ is a y-axis coordinate of the second calibration member in the coordinate system of the mechanical arm;

$x_{p3}$ is an x-axis coordinate of the third coordinate in the coordinate system of the image;

$x_{r3}$ is an x-axis coordinate of the third calibration member in the coordinate system of the mechanical arm;

$y_{p3}$ is a y-axis coordinate of the third calibration member in the coordinate system of the image;

$y_{r3}$ is a y-axis coordinate of the third coordinate on the coordinate system of the mechanical arm;

L is a distance between the first and second calibration members;

θ is a rotation angle of the coordinate system of the image relative to the coordinate system of the mechanical arm; and α is scaling of the image.

Optionally, the first angle is 90°, and in the step of calculating the coordinates of the spherical center of the calibration member in the coordinate system of the mechanical arm, X and Y coordinates of the spherical center of the calibration member in the coordinate system of the mechanical arm are calculated.

Optionally, the step of determining, by the coordinate transformation, the alignment relationship between the coordinate system of the image and the coordinate system of the mechanical arm comprises:

determining the translation parameter by equation (6):

$$\begin{bmatrix} D_x \\ D_z \end{bmatrix} = \begin{bmatrix} x_{p2} \\ z_{p2} \end{bmatrix} - \begin{bmatrix} x_{r2} \\ z_{r2} \end{bmatrix} \quad (6)$$

calculating the rotation parameter by equations (7) to (9):

$$\theta = A - a \quad (7)$$

$$A = \arctan\left[\frac{z_{p3} - z_{p2}}{x_{p3} - x_{p2}}\right] \quad (8)$$

$$a = \arctan\left[\frac{z_{r3} - z_{r2}}{x_{r3} - x_{r2}}\right] \quad (9)$$

$D_x$ is a translation distance of x coordinate of the coordinate system of the image relative to x coordinate of the coordinate system of the mechanical arm;

$D_z$ is a translation distance of z coordinate of the coordinate system of the image relative to z coordinate of the coordinate system of mechanical arm;

$x_{p2}$ is an x-axis coordinate of the second calibration member in the coordinate system of the image;

$x_{r2}$ is an x-axis coordinate of the second calibration member in the coordinate system of the mechanical arm;

$z_{p2}$ is a z-axis coordinate of the second calibration member in the coordinate system of the image;

$z_{r2}$ is a z-axis coordinate of the second calibration member in the coordinate system of the mechanical arm;

$x_{p3}$ is an x-axis coordinate of the third coordinate in the coordinate system of the image;

$x_{r3}$ is an x-axis coordinate of the third calibration member in the coordinate system of the mechanical arm;

$z_{p3}$ is a z-axis coordinate of the third calibration member in the coordinate system of the image;

$z_{r3}$ is a z-axis coordinate of the third calibration member in the coordinate system of the mechanical arm; and θ is a rotation angle of the coordinate system of the image relative to the coordinate system of the mechanical arm.

As a third aspect of the disclosure, there is provided an alignment control device applied to the above therapeutic apparatus according to the disclosure, wherein the alignment control device includes:

a driving mechanism, configured to drive to move the mechanical arm body, so as to move the calibration plate to a position between the image capturing element and the reference plane, wherein the calibration plane is parallel to the reference plane, the calibration plane is located at a level of a treatment site, and an angle between the reference plane and the horizontal plane is a first angle;

a photographing controller, configured to control the image capturing element to obtain an image; and an alignment processor, configured to determine, according to a position of the calibration plane in the obtained image, an alignment relationship between a coordinate system of the image and a coordinate system of the mechanical arm, wherein the coordinate system of the mechanical arm is arranged at the fixed end of the mechanical arm, and a plane X-Y in the coordinate system of the mechanical arm is the horizontal plane.

Optionally, the image capturing element is an X-ray image capturing element, each calibration member is a metal ball, and the alignment processor further includes:

a joint angle determining unit, configured to determine the joint angle information of the mechanical arm body;

an image identification unit, configured to determine the coordinates of the spherical center of each calibration member in the coordinate system of the image;

a coordinate calculation unit, configured to calculate the coordinates of the spherical center of the calibration member in the coordinate system of the mechanical arm; and an alignment unit, configured to determine, by coordinate transformation, the alignment relationship between the coordinate system of the image and the coordinate system of the mechanical arm, wherein the alignment relationship is characterized by a translation parameter of the coordinate system of the image relative to the coordinate system of the mechanical arm, a rotation parameter of the coordinate system of the image relative to the coordinate system of the mechanical arm, and a scaling of the image.

BRIEF DESCRIPTION OF THE DRAWINGS

The accompanying drawings, which are included to provide a further understanding of the disclosure and are incorporated in and constitute a part of this specification, illustrate the disclosure together with the embodiments as set forth below, but do not constitute a limitation of the disclosure. In the drawings.

DETAILED DESCRIPTION OF THE EMBODIMENTS

Hereinafter specific implementations of the disclosure will be described in detail in conjunction to the accompanying drawings. It should be understood that the detailed description and specific implementations are given by way of illustration and explanation only, not limitation.

Figure 1:
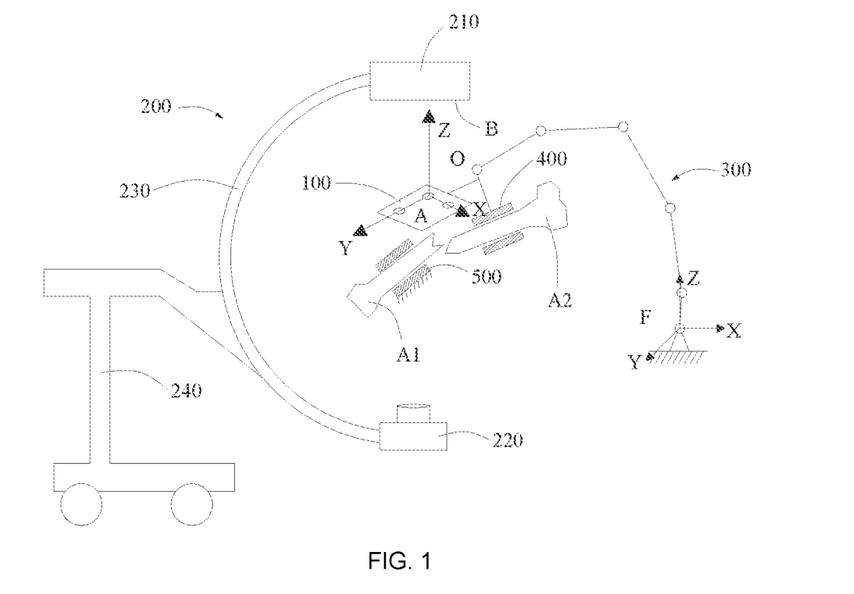
FIG. 1 is a therapeutic apparatus according to the present disclosure at a first treatment position.

As a first aspect of the present disclosure, there is provided a therapeutic apparatus, including an image capturing mechanism 200 and a mechanical arm 300, wherein the therapeutic apparatus, as shown in FIG. 1, further includes a calibration plate 100 on which a calibration plane A is defined.

The image capturing mechanism 200 includes a reference plate 210 and an image capturing element 220 with an adjustable capturing direction, the image capturing element 220 is opposite to and spaced apart from the reference plate 210, and a surface of the reference plate 210 facing the image capturing element 220 is defined as a reference plane B. It should be noted that the relative positional relationship between the reference plate 210 and the image capturing element 220 remains unchanged.

The mechanical arm 300 comprises a mechanical arm body 310, a fixed end F and an operating end O, the fixed end F and the operating end O are located at different positions of the mechanical arm body 300, respectively, the mechanical arm body 310 can be fixed to a mounting base through the fixed end F, the calibration plate 100 is arranged at the operating end O, the mechanical arm body 310 can drive to move the operating end O to a position between the image capturing element 220 and the reference plate 210, and the calibration plate 100 is driven to move to be parallel to the calibration plane A and the reference plane B.

When in treatment with the therapeutic apparatus according to the present disclosure, an alignment between the mechanical arm and an image captured by the image capture element 220 is required first.

During the alignment, it is necessary to move the operating end O to the place between the image capturing element 220 and the reference plate 210 to connect a site to be treated with the operation end O. The position of the calibration plate 100 is adjusted such that a calibration plane A of the calibration plate 100 is parallel to the reference plane B of the reference plate 210, and the calibration plane A of the calibration plate is disposed at the level of the site to be treated.

Since the reference plate 210 is opposed to the image capturing element 220, a photograph taken at the time of alignment includes an image of the calibration plane A and an image of the site to be treated, and a coordinate system of the image is the same as that of the calibration plane A. When the coordinate system of the calibration plane A is aligned to a coordinate system of the mechanical arm, the alignment between the coordinate system in the image captured by the image capturing element 220 and the coordinate system of the mechanical arm can be realized.

After the alignment, the conversion relationship between the coordinate system of the mechanical arm 300 and the coordinate system of the image captured by the image capturing element 220 can be determined, so that a moving distance of the operating end 330 of the mechanical arm 300 and the position to which the operating end is moved can be determined, and a closed reduction can be performed more accurately.

Since the calibration plane is parallel to the reference plane, the coordinates of the calibration plane are the same as those of the image captured by the image capturing element, and since the calibration plate is arranged on the mechanical arm, the alignment relationship between the coordinate systems of the calibration plate and the mechanical arm can be easily determined.

When the alignment method according to the disclosure is used for alignment, three-dimensional reconstruction of images is not desired. A mark point is not necessary to be fixed at a part to be treated, so that additional trauma is not caused and pain of a patient is reduced. The alignment method is simple and convenient to use.

As an alternative embodiment, the alignment includes "normal alignment" and "lateral alignment". Thus, both normal and lateral alignments are required while treatment is being performed with the therapeutic apparatus. Shown in FIG. 1 is a schematic view of a therapeutic apparatus according to the present disclosure when performing a normal alignment. As shown in FIG. 1, the image capturing element 220 and the reference plate 210 are arranged at an interval in the vertical direction, and the calibration plate 100 is arranged at a position having the same level as the part to be treated such that the calibration plane A is parallel to the plane X-Y of the mechanical arm 300. Then an image is captured by the image capturing element 220.

Figure 2:
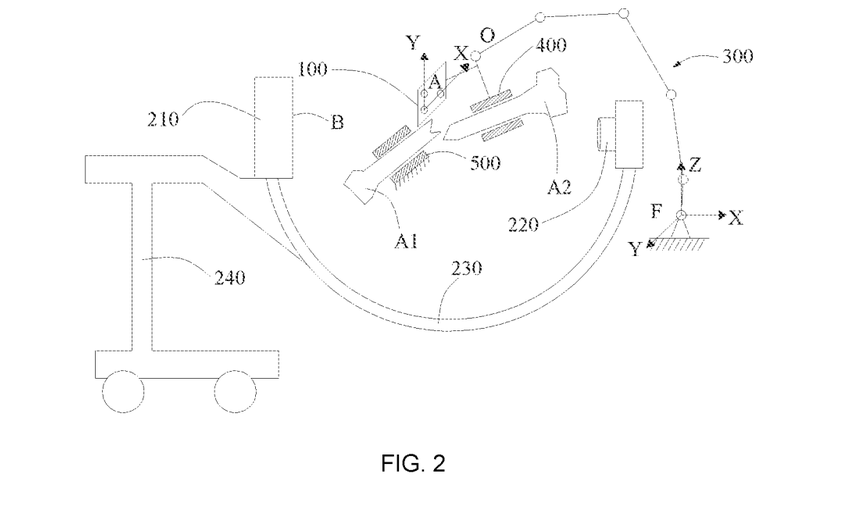
FIG. 2 is the therapeutic apparatus according to the present disclosure at a second treatment position.

Shown in FIG. 2 is a schematic view at the time of lateral alignment. As shown in FIG. 2, the orientation of the calibration plane A of the calibration plate 100 is changed such that the calibration plane A is parallel to the plane X-Z of the mechanical arm. The positions of the image capturing element 220 and the reference plate 210 are adjusted such that the image capturing element 220 and the reference plate 210 are arranged at an interval in the horizontal direction and the reference plane B of the reference plate 210 is parallel to the calibration plane A of the calibration plate 100. Photographing is then performed using the image capturing element 220, and thus the lateral alignment between the coordinates of the image and the coordinates of the mechanical arm 300 is completed.

When the therapeutic apparatus according to the embodiment of the disclosure is used for treatment, the alignment between the coordinates of the image and the coordinates of the mechanical arm can be realized, such that when the mechanical arm is operated, the movement of the mechanical arm is accurately controlled and thus the treatment is more accurately realized.

In the present disclosure, how to arrange the image capturing element 220 and the reference plate 210 is not particularly limited as long as it is possible to ensure that the image capturing element 220 and the reference plate 210 are spaced from each other with the relative positional relationship therebetween unchanged. In order to simplify the structure of the image capturing mechanism, optionally, as shown in FIGS. 1 and 2, the image capturing mechanism further includes a mounting bracket 230 on which the image capturing element 220 and the reference plate 210 are mounted.

In the disclosure, the relative positional relationship between the image capturing element 220 and the reference plate 210 and the mechanical arm 300 can be changed by moving a posture of the image capturing mechanism 200 as a whole.

As an alternative embodiment, the mounting bracket 230 can drive to move the image capturing element 220 and the reference plate 210, so as to change an orientation of the image capturing element 220, and when the image capturing element 220 and the reference plate 210 are moved, the relative positional relationship between the image capturing element 220 and the reference plate 210 remains unchanged.

Figure 3:
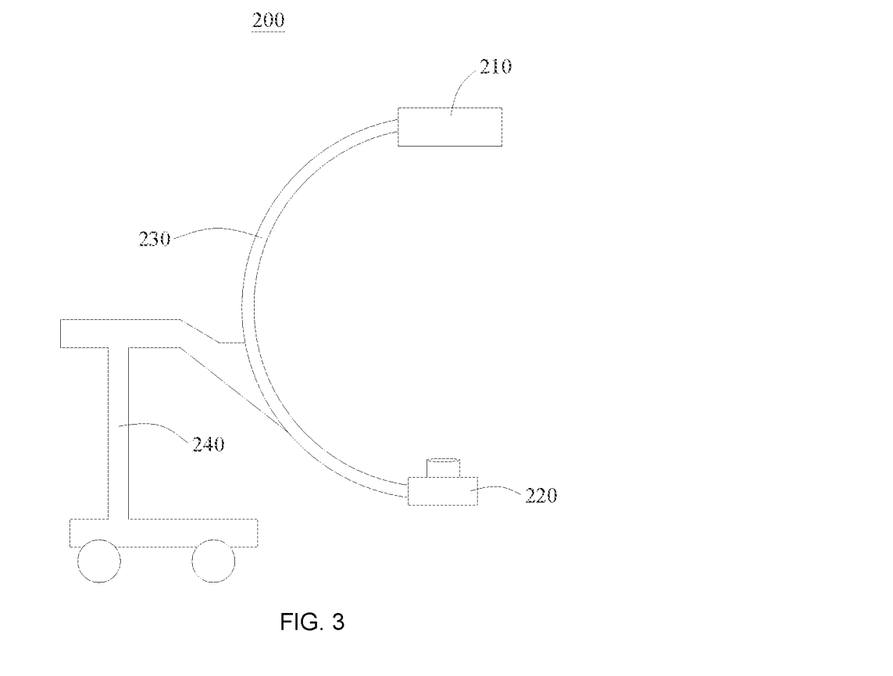
FIG. 3 is a schematic view illustrating a structure of the therapeutic apparatus according to the present disclosure.

In the present disclosure, a specific structure of the mounting bracket is not particularly limited. As shown in FIG. 3, the mounting bracket can include a base 240 and a mounting arm provided on the base 240. The mounting arm includes a mounting arm body 230, a mounting end of reference plate formed on the mounting arm body 230, and a mounting end of image capturing element formed on the mounting arm body 230. The mounting end of reference plate is disposed opposite to and spaced apart from the mounting end of image capturing element. The reference plate 210 is mounted on the mounting end of reference plate, and the image capturing element 220 is mounted on the mounting end of image capturing element.

In the present disclosure, the specific structure of the mounting arm body 230 is not particularly limited. For example, in the embodiment shown as in FIG. 3, the mounting arm body 230 is formed as an arc-shaped rod, the mounting end of the image capturing element 220 is located at an end of the mounting arm body 230, and the mounting end of the reference plate 210 is located at the other end of the mounting arm body 230. The mounting arm body 230 can rotate around a center of the mounting arm body 230 to change the orientation of the image sensor 220.

Since the mounting arm body 230 is a rigid arc-shaped rod, once the image capturing element 220 and the reference plate 210 are mounted on the mounting arm body 230, the relative positional relationship between the image capturing element 220 and the reference plate 210 can be maintained.

In the disclosure, the central angle of the mounting arm body 230 is not particularly limited. As an alternative embodiment, the mounting arm body 230 is a semicircular rod, such that the rotation of the mounting arm body 230 by 90° can realize a switch between the position of normal alignment and the position of lateral alignment.

In the disclosure, how to rotate the mounting arm body 230 around its center is not particularly limited. As an alternative embodiment, a sliding slot is formed on one of the base 240 and the mounting arm body 230, and a projection matching with the sliding slot is formed on the other one of the base 240 and the mounting arm body 230, such that the mounting arm body 230 can rotate on the base 240 about a center of the mounting arm body 230.

Figure 4:
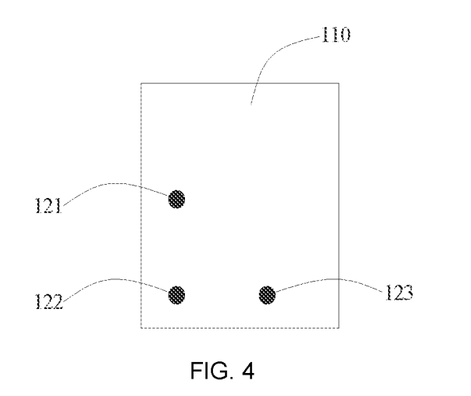
FIG. 4 is a schematic view of a calibration plate.

In the disclosure, the specific structure of the calibration plate 100 is not particularly limited as long as the calibration plate 100 can be photographed by the image capturing element 220. In order to facilitate the identification of the calibration plane A of the calibration plate 100 in the image captured by the image capturing element 220, optionally, as shown in FIG. 4, the calibration plate 100 includes a calibration plate substrate 110 and a plurality of calibration members disposed on the calibration plate substrate 110. The plurality of the calibration members defines the calibration plane.

In the embodiment shown in FIG. 4, the plurality of calibration members provided on the calibration plate 100 are a first calibration member 121, a second calibration member 122 and a third calibration member 123, respectively. Optionally, a first line between the first and second calibration members 121, 123 is perpendicular to a line between the second and third calibration members 122, 123.

By identifying the calibration member in the image captured by the image capture element 220, the coordinate system of the image can be quickly established and aligned with the coordinate system of the robotic arm 300.

In order to facilitate the setting of the calibration plate and avoid the calibration plate from affecting objects (e.g., injured bones) in the image captured by the image capturing element, optionally, the calibration plate substrate 110 is a transparent substrate, and the calibration members are embedded in the calibration plate substrate 110. The calibration plate substrate 110 is not noticeable in the image obtained by the image capturing element 220, such that the position of the calibration members can be easily identified and the image coordinate system can be quickly determined.

The therapeutic apparatus according to the present disclosure may be used for orthopedic treatment, and optionally, the image capturing element 220 can be an X-ray image capturing element, and the calibration members can be metal balls. Alternatively, the calibration plate substrate 110 can be made of plexiglass.

Figure 5:
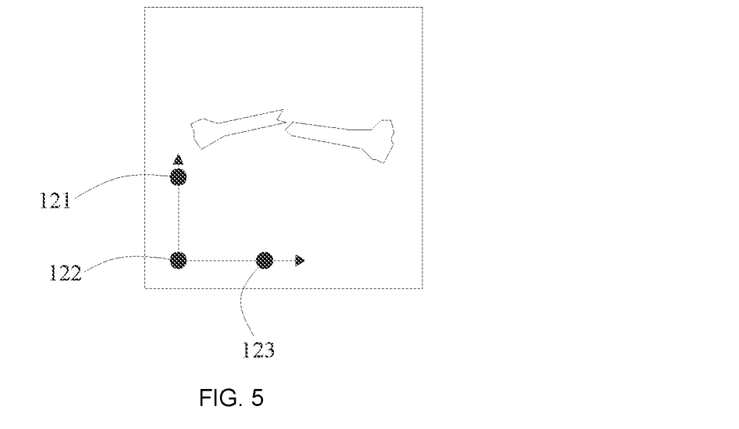
FIG. 5 is a schematic view of a captured image.

From the schematic view of the image taken by the image capturing element 220 as shown in FIG. 5, an image of the bones, an image of the first calibration member 121, an image of the second calibration member 122 and an image of the third calibration member 123 are clearly visible.

The therapeutic apparatus according to the disclosure is particularly suitable for closed reduction of long bone fracture. During the closed reduction, the alignment can be realized only through the calibration plate 100 arranged outside the site to be treated without metal nails at the wounded part, thereby alleviating the pain during the treatment.

In order to facilitate the operation on the treatment site, optionally, the therapeutic apparatus further comprises a clamp 400 disposed at the operating end of the mechanical arm. The clamp 400 can be used to clamp the site to be treated.

Optionally, the therapeutic apparatus can further comprise a support member 500. A patient is supported on the support member 500 and the clamp 400 clamps the site of the patient body during the closed reduction of the long bone fracture using the therapeutic apparatus. Specifically, the first fracture A1 of the long bone is supported on the supporting member 500, and the second fracture A2 of the long bone is clamped by the clamp 400. The therapeutic apparatus, with the use of the medical image taken by the image capturing element 220 as a guide, clamps to move both ends of the fractured bone of the patient through the mechanical arm with multiple degrees of freedom, such that ends of the fractured part are aligned.

Figure 6:
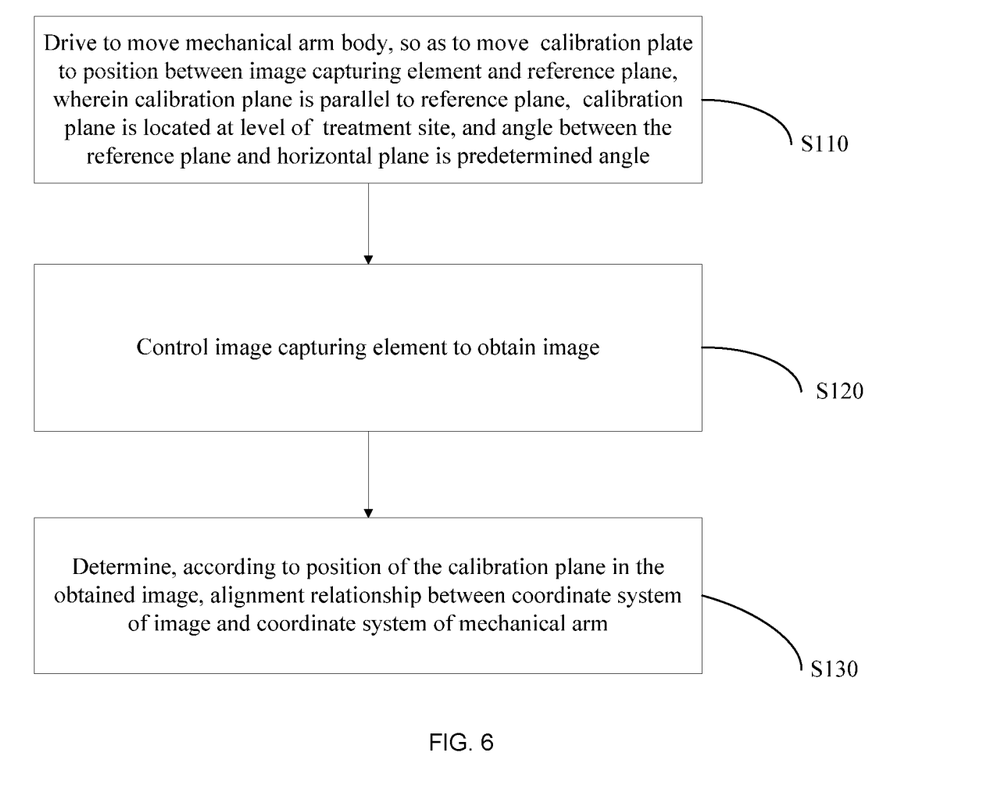
FIG. 6 is a flowchart of an alignment method according to the present disclosure.

As a second aspect of the present disclosure, there is provided an alignment method for the above therapeutic apparatus according to the disclosure. As shown in FIG. 6, the alignment method includes:

In step S110, the mechanical arm body is driven to move so as to move the calibration plate to a position between the image capturing element and the reference plane, wherein the calibration plane is parallel to the reference plane and located at a level of a treatment site, and an angle between the reference plane and the horizontal plane is a first angle;

In step S120, the image capturing element is controlled to obtain an image;

In step S130, an alignment relationship between a coordinate system of the image and a coordinate system of the mechanical arm is determined according to a position of the calibration plane in the captured image, wherein the coordinate system of the mechanical arm is arranged at the fixed end of the mechanical arm, and a plane X-Y in the coordinate system of the mechanical arm is the horizontal plane.

Since the calibration plane is parallel to the reference plane, the calibration plane has the same coordinate as the image captured by the image capturing element. Since the calibration plate is provided on the mechanical arm, the alignment relationship between the calibration plate and the coordinate system of the mechanical arm can be easily determined.

During the alignment using the alignment method according to the disclosure, it is not necessary to perform three-dimensional reconstruction of images and to fix a mark point on a site to be treated, such that no additional trauma is not brought, the pain of a patient is relieved, and the alignment method is simple and convenient to use.

Figure 7:
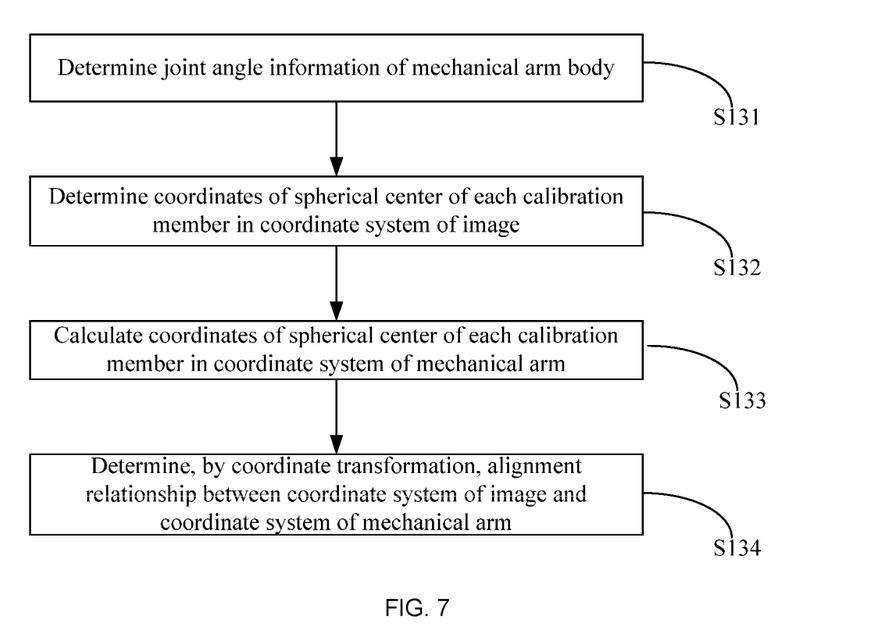
FIG. 7 is a flowchart of step S130 in the alignment method according to the present disclosure.

As described above, as an alternative embodiment, the image capturing element can be an X-ray image capturing element, and each calibration member can be the metal ball. As shown in FIG. 7, the step S130 can include:

In step S131, determining joint angle information of the mechanical arm body;

In step S132, determining coordinates of a spherical center of each calibration member in the coordinate system of the image;

In step S133, calculating coordinates of the spherical center of each calibration member in the coordinate system of the mechanical arm; and In step S134, determining, by coordinate transformation, the alignment relationship between the coordinate system of the image and the coordinate system of the mechanical arm.

As described above, the "alignment" can include "normal alignment" and "lateral alignment". Accordingly, in the alignment method according to the present disclosure, when the first angle is 0°, the reference plane is parallel to the horizontal plane, so that normal alignment can be achieved. Accordingly, in step 133, X and Y coordinates of the spherical center of the calibration member in the coordinate system of the mechanical arm are calculated.

It can be obtained by image identification that the coordinates of the center of sphere of the second calibration member 122 in the coordinate system of the image (in a unit of pixel) are $(x_{p2}, y_{p2})$, and the coordinates of the center of sphere of the third calibration member 123 in the coordinate system of the image are $(x_{p3}, y_{p3})$.

According to the mounting position of the calibration plate on the mechanical arm, it can be obtained that X and Y values of the coordinates of the spherical center of the second calibration member 122 in the coordinate system of the mechanical arm are $(x_{r2}, y_{r2})$, and X and Y values of the coordinates of the spherical center of the third calibration member 123 in the coordinate system of the mechanical arm are $(x_{r3}, y_{r3})$.

An actual physical distance between the second calibration member 122 and the first calibration member 121 is L, and thus scaling of the image to the real world is represented as $\alpha = |x_{p2}|/L$. According to the scaling a and the representations $(x_{p2}, y_{p2})$, $(x_{p3}, y_{p3})$, $(x_{r2}, y_{r2})$ and $(x_{r3}, y_{r3})$ of the second and third calibration members 122, 123 in coordinate systems of the image and the mechanical arm, respectively, an alignment relationship between the coordinate system of the image and X-Y coordinate system of the mechanical arm can be obtained by using the existing two-dimensional coordinate transformation algorithm.

Common two-dimensional coordinate transformation algorithms include the direct parameter method, the least square method and the like. Since the coordinates of two common points of the second and third calibration members 122 and 123 are only used in the present disclosure, the direct parameter method is suitable. The implementation steps thereof are as follows:

Translation parameter is calculated by equation (1):

$$\begin{bmatrix} D_x \\ D_y \end{bmatrix} = \begin{bmatrix} x_{p2} \\ y_{p2} \end{bmatrix} - \begin{bmatrix} x_{r2} \\ y_{r2} \end{bmatrix} \quad (1)$$

Rotation parameter is calculated by equations (2) to (4):

$$\theta = A - a \quad (2)$$

$$A = \arctan\left[\frac{y_{p3} - y_{p2}}{x_{p3} - x_{p2}}\right] \quad (3)$$

$$a = \arctan\left[\frac{y_{r3} - y_{r2}}{x_{r3} - x_{r2}}\right] \quad (4)$$

Scaling of the image is calculated by equation (5):

$$\alpha = \frac{|x_{p2}|}{L} \quad (5)$$

Here, $D_x$ is a translation distance of x coordinate of the coordinate system of the image relative to x coordinate of the coordinate system of the mechanical arm, and $D_y$ is a translation distance of y coordinate of the coordinate system of the image relative to y coordinate of the coordinate system of mechanical arm;
  $x_{p2}$ is an x-axis coordinate of the second calibration member in the coordinate system of the image;
  $x_{r2}$ is an x-axis coordinate of the second calibration member in the coordinate system of the mechanical arm;
  $y_{p2}$ is a y-axis coordinate of the second calibration member in the coordinate system of the image;
  $y_{r2}$ is a y-axis coordinate of the second calibration member in the coordinate system of the mechanical arm;
  $x_{p3}$ is an x-axis coordinate of the third coordinate in the coordinate system of the image;
  $x_{r3}$ is an x-axis coordinate of the third calibration member in the coordinate system of the mechanical arm;
  $y_{p3}$ is a y-axis coordinate of the third calibration member in the coordinate system of the image;
  $y_{r3}$ is a y-axis coordinate of the third coordinate on the coordinate system of the mechanical arm;
  L is a distance between the first and second calibration members;
  $\theta$ is a rotation angle of the coordinate system of the image relative to the coordinate system of the mechanical arm; and
  $\alpha$ is scaling of the image.

In the lateral alignment, the first angle is 90°, and in the step of calculating the coordinates of the spherical center of the calibration member in the coordinate system of the mechanical arm, the X-coordinate and the Z-coordinate of the spherical center of the calibration member in the coordinate system of the mechanical arm are calculated.

It can be obtained by image identification that the coordinates of the center of sphere of the second calibration member 122 in the coordinate system of the image (in a unit of pixel) are $(x_{p2}, z_{p2})$, and the coordinates of the center of sphere of the third calibration member 123 in the coordinate system of the image are $(x_{p3}, z_{p3})$.

According to the mounting position of the calibration plate on the mechanical arm, it can be obtained that X and Z values of the coordinates of the spherical center of the second calibration member 122 in the coordinate system of the mechanical arm are $(x_{r2}, z_{r2})$, and X and Z values of the coordinates of the spherical center of the third calibration member 123 in the coordinate system of the mechanical arm are $(x_{r3}, z_{r3})$.

An actual physical distance of the second calibration member 122 and the first calibration member 121 is L, and thus scaling of the image to the real world is represented as $\alpha=|x_{p2}|/L$. According to the scaling a and the representations $(x_{p2}, z_{p2})$, $(x_{p3}, z_{p3})$, $(x_{r2}, z_{r2})$ and $(x_{r3}, z_{r3})$ of the second and third calibration members 122, 123 in coordinate systems of the image and the mechanical arm, respectively, an alignment relationship between the coordinate system of the image and X-Z coordinate system of the mechanical arm can be obtained by using the existing two-dimensional coordinate transformation algorithm.

Translation parameter is determined by equation (6);

$$\begin{bmatrix} D_x \\ D_z \end{bmatrix} = \begin{bmatrix} x_{p2} \\ z_{p2} \end{bmatrix} - \begin{bmatrix} x_{r2} \\ z_{r2} \end{bmatrix} \quad (6)$$

Rotation parameter is calculated by equations (7) to (9):

$$\theta = A - a \quad (7)$$

$$A = \arctan\left[\frac{z_{p3} - z_{p2}}{x_{p3} - x_{p2}}\right] \quad (8)$$

$$a = \arctan\left[\frac{z_{r3} - z_{r2}}{x_{r3} - x_{r2}}\right] \quad (9)$$

$D_x$ is a translation distance of x coordinate of the coordinate system of the image relative to x coordinate of the coordinate system of the mechanical arm;
  $D_z$ is a translation distance of z coordinate of the coordinate system of the image relative to z coordinate of the coordinate system of mechanical arm;
  $x_{p2}$ is an x-axis coordinate of the second calibration member in the coordinate system of the image;
  $x_{r2}$ is an x-axis coordinate of the second calibration member in the coordinate system of the mechanical arm;
  $z_{p2}$ is a z-axis coordinate of the second calibration member in the coordinate system of the image;
  $z_{r2}$ is a z-axis coordinate of the second calibration member in the coordinate system of the mechanical arm;
  $x_{p3}$ is an x-axis coordinate of the third coordinate in the coordinate system of the image;
  $x_{r3}$ is an x-axis coordinate of the third calibration member in the coordinate system of the mechanical arm;
  $z_{p3}$ is a z-axis coordinate of the third calibration member in the coordinate system of the image;

$z_{r3}$ is a z-axis coordinate of the third calibration member in the coordinate system of the mechanical arm;

L is a distance between the first and second calibration members; and

θ is a rotation angle of the coordinate system of the image relative to the coordinate system of the mechanical arm.

It is noted that the alignment is not limited to the two aspects of "normal alignment" and "lateral alignment" as described above. In the situation where the site to be treated is complex, alignment of other sites can be introduced. That is, the first angle can be other than 0° and 90°.

Figure 8:
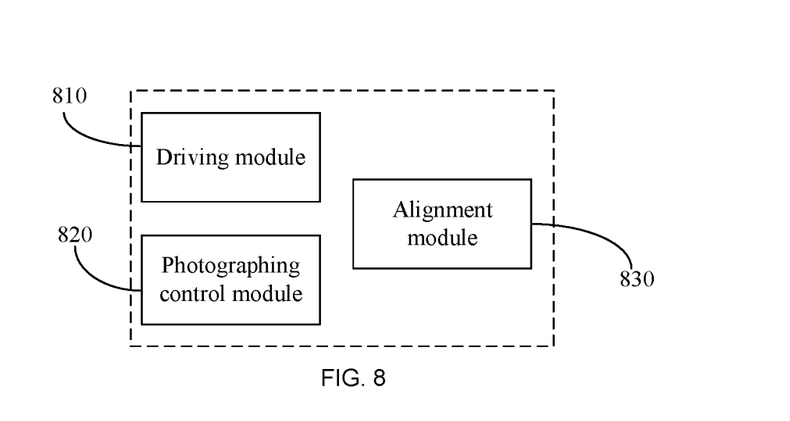
FIG. 8 is a diagram schematically illustrating modules of an alignment apparatus according to the present disclosure.

As a third aspect of the present disclosure, there is provided an alignment control device, applicable to the above-mentioned therapeutic apparatus provided in the disclosure. As shown in FIG. 8, the alignment control device includes a driving mechanism 810, a photographing controller 820, and an alignment processor 830.

The driving mechanism 810 is configured to drive to move the mechanical arm body, so as to move the calibration plate to a position between the image capturing element and the reference plane, wherein the calibration plane is parallel to the reference plane, the calibration plane is located at a level of a treatment site, and an angle between the reference plane and the horizontal plane is a first angle.

The photographing controller 820 is configured to control the image capturing element to obtain an image.

The alignment processor 830 is configured to determine the alignment relationship between coordinate systems of the image and the mechanical arm according to a position of the calibration plane in the captured image, wherein the coordinate system of the mechanical arm is disposed at a fixed end of the mechanical arm, and a plane X-Y in the coordinate system of the mechanical arm is the horizontal plane.

The alignment control device is configured to perform the above alignment method according to the present disclosure, and the working principle of the alignment method has been described in detail above, which is not described herein again.

In the disclosure, the specific structure of the driving mechanism 810 is not particularly limited. The drive mechanism 810 can be selected from any one of a hydraulic drive mechanism, a pneumatic drive mechanism, an electrical drive mechanism, and a mechanical drive mechanism.

In the present disclosure, the specific structure of the photographing controller 820 is also not particularly limited. The photographing controller 820 can be an electric shutter, for example. When the electric shutter receives a photographing signal sent from an upper machine (for example, a computer controlled by an operator), the electric shutter can act to enable the image capturing element to start photographing.

In the present disclosure, the specific structure of the alignment processor 830 is not particularly limited, and the alignment processor can be a chip with computing power.

Figure 9:
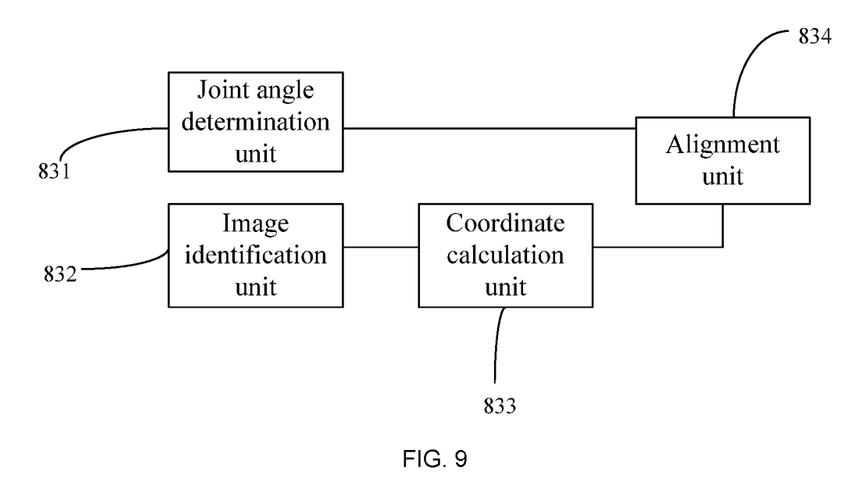
FIG. 9 is a schematic diagram of an alignment processor in the alignment apparatus according to the present disclosure.

Optionally, the image capturing element is an X-ray image capturing element, the calibration members are metal balls. As shown in FIG. 9, the alignment processor 830 includes a joint angle determination unit 831, an image identification unit 832, a coordinate calculation unit 833 and an alignment unit 834.

The joint angle determination unit 831 is configured to determine joint angle information of the mechanical arm body.

The image identification unit 832 is configured to determine the coordinates of the spherical center of each of the calibration members in the coordinate system of the image.

The coordinate calculation unit 833 is configured to calculate the coordinates of the spherical center of the calibration member in the coordinate system of the mechanical arm.

The alignment unit 834 is configured to determine an alignment relationship between the coordinate system of the image and the coordinate system of the mechanical arm by coordinate transformation, wherein the alignment relationship is characterized by a translation parameter of the coordinate system of the image relative to the coordinate system of the mechanical arm, a rotation parameter of the coordinate system of the image relative to the coordinate system of the mechanical arm, and a scaling of the image.

Optionally, the first angle is 0°, and the coordinate calculation unit is configured to calculate an X coordinate and a Y coordinate of a spherical center of the calibration member in the coordinate system of the mechanical arm.

Optionally, the alignment unit is configured to determine the alignment relationship between the coordinate system of the image and the coordinate system of the mechanical arm by:

calculating the translation parameters by equation (1):

$$\begin{bmatrix} D_x \\ D_y \end{bmatrix} = \begin{bmatrix} x_{p2} \\ y_{p2} \end{bmatrix} - \begin{bmatrix} x_{r2} \\ y_{r2} \end{bmatrix} \quad (1)$$

calculating the rotation parameter by equations (2) to (4):

$$\theta = A - a \quad (2)$$

$$A = \arctan\left[\frac{y_{p3} - y_{p2}}{x_{p3} - x_{p2}}\right] \quad (3)$$

$$a = \arctan\left[\frac{y_{r3} - y_{r2}}{x_{r3} - x_{r2}}\right] \quad (4)$$

calculating the scaling of the image by equation (5):

$$\alpha = \frac{|x_{p2}|}{L} \quad (5)$$

Here, $D_x$ is a translation distance of x coordinate of the coordinate system of the image relative to x coordinate of the coordinate system of the mechanical arm, and $D_y$ is a translation distance of y coordinate of the coordinate system of the image relative to y coordinate of the coordinate system of mechanical arm;

$x_{p2}$ is an x-axis coordinate of the second calibration member in the coordinate system of the image;

$x_{r2}$ is an x-axis coordinate of the second calibration member in the coordinate system of the mechanical arm;

$y_{p2}$ is a y-axis coordinate of the second calibration member in the coordinate system of the image;

$y_{r2}$ is a y-axis coordinate of the second calibration member in the coordinate system of the mechanical arm;

$x_{p3}$ is an x-axis coordinate of the third coordinate in the coordinate system of the image;

$x_{r3}$ is an x-axis coordinate of the third calibration member in the coordinate system of the mechanical arm;

$y_{p3}$ is a y-axis coordinate of the third calibration member in the coordinate system of the image;

$y_{r3}$ is a y-axis coordinate of the third coordinate on the coordinate system of the mechanical arm;

L is a distance between the first and second calibration members;

θ is a rotation angle of the coordinate system of the image relative to the coordinate system of the mechanical arm; and α is scaling of the image.

Optionally, the first angle is 90°, and the calculation unit is configured to calculate the X coordinate and the Z coordinate of the spherical center of the calibration member in the coordinate system of the mechanical arm.

Optionally, the alignment unit is configured to determine the alignment relationship between the coordinate system of the image and the coordinate system of the mechanical arm by:

determining the translation parameter by using equation (6);

$$\begin{bmatrix} D_x \\ D_z \end{bmatrix} = \begin{bmatrix} x_{p2} \\ z_{p2} \end{bmatrix} - \begin{bmatrix} x_{r2} \\ z_{r2} \end{bmatrix} \quad (6)$$

calculating the rotation parameter by equations (7) to (9):

$$\theta = A - a \quad (7)$$

$$A = \arctan\left[\frac{z_{p3} - z_{p2}}{x_{p3} - x_{p2}}\right] \quad (8)$$

$$a = \arctan\left[\frac{z_{r3} - z_{r2}}{x_{r3} - x_{r2}}\right] \quad (9)$$

$D_x$ is a translation distance of x coordinate of the coordinate system of the image relative to x coordinate of the coordinate system of the mechanical arm;

$D_z$ is a translation distance of z coordinate of the coordinate system of the image relative to z coordinate of the coordinate system of mechanical arm;

$x_{p2}$ is an x-axis coordinate of the second calibration member in the coordinate system of the image;

$x_{r2}$ is an x-axis coordinate of the second calibration member in the coordinate system of the mechanical arm;

$z_{p2}$ is a z-axis coordinate of the second calibration member in the coordinate system of the image;

$z_{r2}$ is a z-axis coordinate of the second calibration member in the coordinate system of the mechanical arm;

$x_{p3}$ is an x-axis coordinate of the third coordinate in the coordinate system of the image;

$x_{r3}$ is an x-axis coordinate of the third calibration member in the coordinate system of the mechanical arm;

$z_{p3}$ is a z-axis coordinate of the third calibration member in the coordinate system of the image;

$z_{r3}$ is a z-axis coordinate of the third calibration member in the coordinate system of the mechanical arm; and θ is a rotation angle of the coordinate system of the image relative to the coordinate system of the mechanical arm.

It will be understood that the above embodiments are merely exemplary embodiments employed to illustrate the principles of the present disclosure, and the present disclosure is not limited thereto. It will be apparent to those skilled in the art that various changes and modifications can be made therein without departing from the spirit and scope of the disclosure, and these changes and modifications should be considered within the scope of the disclosure.

The invention claimed is:

1. A therapeutic apparatus, comprising an image capturing mechanism and a mechanical arm, wherein
the therapeutic apparatus further comprises a calibration plate on which a calibration plane is defined;
the image capturing mechanism includes a reference plate and an imager with an adjustable capturing direction, the imager is opposite to and spaced apart from the reference plate, and a surface of the reference plate facing the imager is defined as a reference plane; and
the mechanical arm includes a mechanical arm body, a fixed end and an operating end, the fixed end and the operating end are located at different positions of the mechanical arm body, respectively, the mechanical arm body is able to be fixed to a mounting base through the fixed end, the calibration plate is arranged at the operating end, and the mechanical arm body is able to drive to move the operating end to a position between the imager and the reference plate such that the calibration plate is driven to move to be parallel to the calibration plane and the reference plane.

2. The therapeutic apparatus according to claim 1, wherein the calibration plate comprises a calibration plate substrate and a plurality of calibration members provided on the calibration plate substrate, the plurality of calibration members defining the calibration plane.

3. The therapeutic apparatus according to claim 2, wherein the plurality of calibration members comprises a first calibration member, a second calibration member and a third calibration member, a first line between the first calibration member and the second calibration member being perpendicular to a third line between the second calibration member and the third calibration member.

4. The therapeutic apparatus according to claim 2, wherein the calibration plate substrate is a transparent substrate, and the calibration members are embedded in the calibration plate substrate.

5. The therapeutic apparatus according to claim 4, wherein the imager is an X-ray imager and each calibration member is a metal ball.

6. The therapeutic apparatus according to claim 1, further comprising a clamp disposed at the operating end of the mechanical arm.

7. The therapeutic apparatus according to claim 1, wherein the image capturing mechanism further comprises a mounting bracket on which the imager and the reference plate are mounted.

8. The therapeutic apparatus according to claim 7, wherein the mounting bracket is able to drive to move the imager and the reference plate to change an orientation of the imager, and when the imager and the reference plate are moved, a relative positional relationship between the imager and the reference plate is kept unchanged.

9. The therapeutic apparatus according to claim 8, wherein the mounting bracket comprises a base and a mounting arm disposed on the base, the mounting arm includes a mounting arm body, a mounting end of reference plate formed on the mounting arm body and a mounting end of the image capture element formed on the mounting arm body, the mounting end of the reference plate is disposed opposite to and spaced apart from the mounting end of the image capture element, the reference plate is mounted on the mounting end of the reference plate, and the image capture element is mounted on the mounting end of the image capture element.

10. The therapeutic apparatus according to claim 9, wherein the mounting arm body is formed as an arc-shaped rod, the mounting end of the imager is located at an end of the mounting arm body, the mounting end of the reference plate is located at the other end of the mounting arm body, and the mounting arm body is rotatable around a center of the mounting arm body to change the orientation of the imager.

11. The therapeutic apparatus according to claim 10, wherein one of the base and the mounting arm body is formed with a sliding slot and the other one of the base and the mounting arm body is formed with a projection that matches with the slide slot, allowing the mounting arm body to rotate on the base about a center of the mounting arm body.

12. An alignment method applied to the therapeutic apparatus according to claim 2, wherein the alignment method comprises:
driving to move the mechanical arm body, so as to move the calibration plate to a position between the imager and the reference plane, wherein the calibration plane is parallel to the reference plane and located at a level of a treatment site, and an angle between the reference plane and a horizontal plane is a first angle;
controlling the imager to obtain an image; and
determining, according to a position of the calibration plane in the obtained image, an alignment relationship between a coordinate system of the image and a coordinate system of the mechanical arm, wherein the coordinate system of the mechanical arm is arranged at the fixed end of the mechanical arm, and a plane X-Y in the coordinate system of the mechanical arm is the horizontal plane.

13. The alignment method according to claim 12, wherein the imager is an X-ray imager, each calibration member is a metal ball, the plurality of calibration members comprise a first calibration member, a second calibration member and a third calibration member, and a first line between the first calibration member and the second calibration member is perpendicular to a third line between the second calibration member and the third calibration member, and
wherein the step of determining, according to the position of the calibration plane in the obtained image, the alignment relationship between the coordinate system of the image and the coordinate system of the mechanical arm comprises:
determining joint angle information of the mechanical arm body;
determining coordinates of a spherical center of each calibration member in the coordinate system of the image;
calculating coordinates of the spherical center of each calibration member in the coordinate system of the mechanical arm; and
determining, by coordinate transformation, the alignment relationship between the coordinate system of the image and the coordinate system of the mechanical arm, wherein the alignment relationship is characterized by a translation parameter of the coordinate system of the image relative to the coordinate system of the mechanical arm, a rotation parameter of the coordinate system of the image relative to the coordinate system of the mechanical arm, and scaling of the image.

14. The alignment method according to claim 13, wherein the first angle is 0°, and in the step of calculating coordinates of the spherical center of each calibration member in the coordinate system of the mechanical arm, X and Y coordinates of the spherical center of the calibration member in the coordinate system of the mechanical arm are calculated.

15. The alignment method according to claim 14, wherein the step of determining, by the coordinate transformation, the alignment relationship between the coordinate system of the image and the coordinate system of the mechanical arm comprises:
determining the translation parameter by equation (1):

$$\begin{bmatrix} D_x \\ D_y \end{bmatrix} = \begin{bmatrix} x_{p2} \\ y_{p2} \end{bmatrix} - \begin{bmatrix} x_{r2} \\ y_{r2} \end{bmatrix} \qquad (1)$$

calculating the rotation parameter by equations (2) to (4):

$$\theta = A - a \qquad (2)$$

$$A = \arctan\left[\frac{y_{p3} - y_{p2}}{x_{p3} - x_{p2}}\right] \qquad (3)$$

$$a = \arctan\left[\frac{y_{r3} - y_{r2}}{x_{r3} - x_{r2}}\right] \qquad (4)$$

calculating the scaling of the image by equation (5):

$$\alpha = \frac{|x_{p2}|}{L} \qquad (5)$$

wherein $D_x$ is a translation distance of x coordinate of the coordinate system of the image relative to x coordinate of the coordinate system of the mechanical arm, and $D_y$ is a translation distance of y coordinate of the coordinate system of the image relative to y coordinate of the coordinate system of mechanical arm;
$x_{p2}$ is an x-axis coordinate of the second calibration member in the coordinate system of the image;
$x_{r2}$ is an x-axis coordinate of the second calibration member in the coordinate system of the mechanical arm;
$y_{p2}$ is a y-axis coordinate of the second calibration member in the coordinate system of the image;
$y_{r2}$ is a y-axis coordinate of the second calibration member in the coordinate system of the mechanical arm;
$x_{p3}$ is an x-axis coordinate of the third coordinate in the coordinate system of the image;
$x_{r3}$ is an x-axis coordinate of the third calibration member in the coordinate system of the mechanical arm;
$y_{p3}$ is a y-axis coordinate of the third calibration member in the coordinate system of the image;
$y_{r3}$ is a y-axis coordinate of the third coordinate on the coordinate system of the mechanical arm;
L is a distance between the first and second calibration members;
θ is a rotation angle of the coordinate system of the image relative to the coordinate system of the mechanical arm; and
α is scaling of the image.

16. The alignment method according to claim 13, wherein the first angle is 90°, and in the step of calculating the coordinates of the spherical center of the calibration member in the coordinate system of the mechanical arm, X and Z coordinates of the spherical center of the calibration member in the coordinate system of the mechanical arm are calculated.

17. The alignment method according to claim 16, wherein the step of determining, by the coordinate transformation, the alignment relationship between the coordinate system of the image and the coordinate system of the mechanical arm comprises:

determining the translation parameter by equation (6):

$$\begin{bmatrix} D_x \\ D_z \end{bmatrix} = \begin{bmatrix} x_{p2} \\ z_{p2} \end{bmatrix} - \begin{bmatrix} x_{r2} \\ z_{r2} \end{bmatrix} \qquad (6)$$

calculating the rotation parameter by equations (7) to (9):

$$\theta = A - a \qquad (7)$$

$$A = \arctan\left[\frac{z_{p3} - z_{p2}}{x_{p3} - x_{p2}}\right] \qquad (8)$$

$$a = \arctan\left[\frac{z_{r3} - z_{r2}}{x_{r3} - x_{r2}}\right] \qquad (9)$$

$D_x$ is a translation distance of x coordinate of the coordinate system of the image relative to x coordinate of the coordinate system of the mechanical arm;

$D_z$ is a translation distance of z coordinate of the coordinate system of the image relative to z coordinate of the coordinate system of mechanical arm;

$x_{p2}$ is an x-axis coordinate of the second calibration member in the coordinate system of the image;

$x_{r2}$ is an x-axis coordinate of the second calibration member in the coordinate system of the mechanical arm;

$z_{p2}$ is a z-axis coordinate of the second calibration member in the coordinate system of the image;

$z_{r2}$ is a z-axis coordinate of the second calibration member in the coordinate system of the mechanical arm;

$x_{p3}$ is an x-axis coordinate of the third coordinate in the coordinate system of the image;

$x_{r3}$ is an x-axis coordinate of the third calibration member in the coordinate system of the mechanical arm;

$z_{p3}$ is a z-axis coordinate of the third calibration member in the coordinate system of the image;

$z_{r3}$ is a z-axis coordinate of the third calibration member in the coordinate system of the mechanical arm; and $\theta$ is a rotation angle of the coordinate system of the image relative to the coordinate system of the mechanical arm.

18. An alignment control device, applied to the therapeutic device according to claim 2, wherein the alignment control device comprises:

a driving mechanism, configured to drive to move the mechanical arm body, so as to move the calibration plate to a position between the imager and the reference plane, wherein the calibration plane is parallel to the reference plane, the calibration plane is located at a level of a treatment site, and an angle between the reference plane and a horizontal plane is a first angle;

a photographing controller, configured to control the imager to obtain an image; and an alignment processor, configured to determine, according to a position of the calibration plane in the obtained image, an alignment relationship between a coordinate system of the image and a coordinate system of the mechanical arm, wherein the coordinate system of the mechanical arm is arranged at the fixed end of the mechanical arm, and a plane X-Y in the coordinate system of the mechanical arm is the horizontal plane.

19. A non-transitory computer-readable storage medium, storing a computer program, wherein when executed by a processor, the computer program carries out the method according to claim 12.

* * * * *